United States Patent [19]

Franz et al.

[11] Patent Number: 5,527,831
[45] Date of Patent: Jun. 18, 1996

[54] PHARMACEUTICAL COMPOSITION FOR TOPICAL APPLICATION TO THE EYE FOR TREATING INCREASED INTRAOCULAR PRESSURE

[75] Inventors: Helmut Franz; Hannes E. Kompa; Tibor Rozman, all of Biberach, Germany

[73] Assignee: Basotherm GmbH, Biberach, Germany

[21] Appl. No.: 109,417

[22] Filed: Aug. 19, 1993

[30] Foreign Application Priority Data

Sep. 4, 1992 [DE] Germany ............ 42 29 494.0

[51] Int. Cl.⁶ .................................................. A61K 31/045
[52] U.S. Cl. .................................. 514/738; 514/913
[58] Field of Search ................................ 514/738, 913

[56] References Cited

FOREIGN PATENT DOCUMENTS

| | | |
|---|---|---|
| 2661832 | 11/1991 | France . |
| 3119051 | 3/1982 | Germany . |
| 3700379 | 7/1986 | Germany . |
| 3734835 | 6/1988 | Germany . |
| 2072015 | 9/1981 | United Kingdom . |

OTHER PUBLICATIONS

Medline Abstract 68397020, (1967).Smolarz–Dudarewicz.

Medline Abstract 66165575 (1965).Okuda et al.

*Primary Examiner*—Zohreh Fay
*Attorney, Agent, or Firm*—Robert P. Raymond; Wendy E. Rieder; Alan R. Stempel

[57] ABSTRACT

The invention relates to an ophthalmic solution for topical application to the eye in order to lower increased intraocular pressure of the aqueous humor, containing a quantity of a polyhydroxyalcohol such as sorbitol, mannitol, inositol or xylitol or mixtures thereof, effective for lowering the intraocular pressure of aqueous humor, in a carrier tolerated by the eye, the use thereof and the preparation thereof.

9 Claims, 1 Drawing Sheet

PHARMACEUTICAL COMPOSITION FOR TOPICAL APPLICATION TO THE EYE FOR TREATING INCREASED INTRAOCULAR PRESSURE

FIELD OF THE INVENTION

The present invention relates to a pharmaceutical composition for topical use on the eye for treating increased intraocular pressure.

BACKGROUND OF THE INVENTION

Increased intraocular pressure can lead to damage to the optic nerve and consequently to a restriction of vision, taking the form of a slowly increasing restriction to the field of vision and possibly leading to blindness if treatment is neglected. The cause of this disease resides in an imbalance between the production of aqueous humour and the corresponding drainage system.

The production of aqueous humour is effected through the vascular system of the uvea, particularly through the vascular system of the ciliary bodies and the epithelial cells of the ciliary body. The aqueous humour is drained away through the trabecular system. The following pathological mechanisms are involved in producing increased intraocular pressure:

A partial drainage obstruction in the trabecular system caused by fibrosing or by increased resistance of the drainage vessels.

Increased perfusion pressure (filtration pressure) of the ciliary vessels and obstructed flow caused by increased resistance of the venoles lead to an increased production of aqueous humour.

Breaching of the blood-water barrier of the uveal vascular system with an escape of plasma and an increase in the colloid osmotic pressure, as a result of which more water is formed in compensation. Disorders of the intraocular blood-water barrier also frequently occur after intraocular operations, e.g. after trabeculectomy or cataract operations.

If the increased intraocular pressure is treated with β-blockers which bring about a reduced production of aqueous humour by vasoconstriction of the vascular system of the uvea, this has the side effect of negatively influencing the ocular blood flow (A. Yoshida, G. T. Feke et al., Ophthalmic. Res. 23, 162–170 (1991) and M. Langham, Arvo Meeting 1992, Sarasota). This disadvantageous effect is not encountered when compounds with an osmoregulatory effect are used.

The oral or intravenous administration described in the literature of hypertonic substances, such as urea or polyalcohols, which have an osmotic effect on the intraocular fluid, involves, to some extent, considerable systemic side effects. P. Segal and J. Smolarz-Dudarewicz describe, in Klin. Monatsbl. Augenheilkd. 150, 509–522 (1967) the effect of glycerol, mannitol and sorbitol in lowering pressure in the eye, when administered orally. In the case of glycerol, the predominant side effects are the effects on the central nervous system, which can be put down to the osmotic activity of the drug, such as headaches, drowsiness and feeling of dizziness, whereas the use of mannitol and sorbitol additionally often lead to diarrhoea.

When mannitol was administered intravenously, in addition to dizziness, headache and shivering, respiratory problems were also caused, with cyanosis and coldness of the limbs and, particularly in patients with renal and cardiac insufficiency, there was also precordial pain with changes in the ECG curve and, in individual cases, fulminating heart failure. Side effects described for the intravenous use of urea solutions are loss of appetite, nausea, a rise in temperature, electrocardiographic changes and pulmonary oedema, which means that such therapy is contraindicated for patients with liver, renal and cardiac circulatory insufficiency (cf. G. B. Bietti, Klin. Monatsbl. Augenheilkd. 150, 317–324 (1967)).

The treatment of increased intraocular pressure by the intravenous infusion of sorbitol solutions, described as long ago as 1938, has also not been generally adopted [J. Bellows et al., J. Arch. Ophth. (A.M.A.) 20, 1036–1043 (1938)].

For this reason it would be desirable to develop a method of treating increased intraocular pressure in which, by topical application to the eye, it is possible to achieve a targeted drainage of humour locally restricted to the desired site and thereby lowering the intraocular pressure, thus avoiding the above-mentioned systemic side effects of compounds with an osmoregulatory activity, and having no negative effect on ocular blood flow.

U.S. Pat. No. 4,201,706 describes a method of reducing corneal oedema which consists in the topical application of an aqueous ophthalmic solution which contains as active substance a penta- or hexahydroxyalcohol such as sorbitol, inositol or xylitol. Corneal oedema can be produced by physical trauma or by irritations and is also observed in conjunction with diseases such as glaucoma.

BRIEF DESCRIPTION OF THE INVENTION

It has now been found that the topical application of an ophthalmic solution containing as active substance a therapeutically effective amount of a polyhydroxyalcohol such as sorbitol, mannitol, inositol and xylitol or mixtures thereof, in a carrier which is tolerated by the eye can significantly reduce increased intraocular pressure, whilst the above-mentioned systemic side effects of compounds with an osmoregulatory effect are avoided by the locally restricted application and the low concentration of the active substance and, as a result of the absence of any vasoconstrictory properties of the active substance, there is no negative effect on the ocular blood flow.

DETAILED DESCRIPTION OF THE INVENTION

Figure 1:
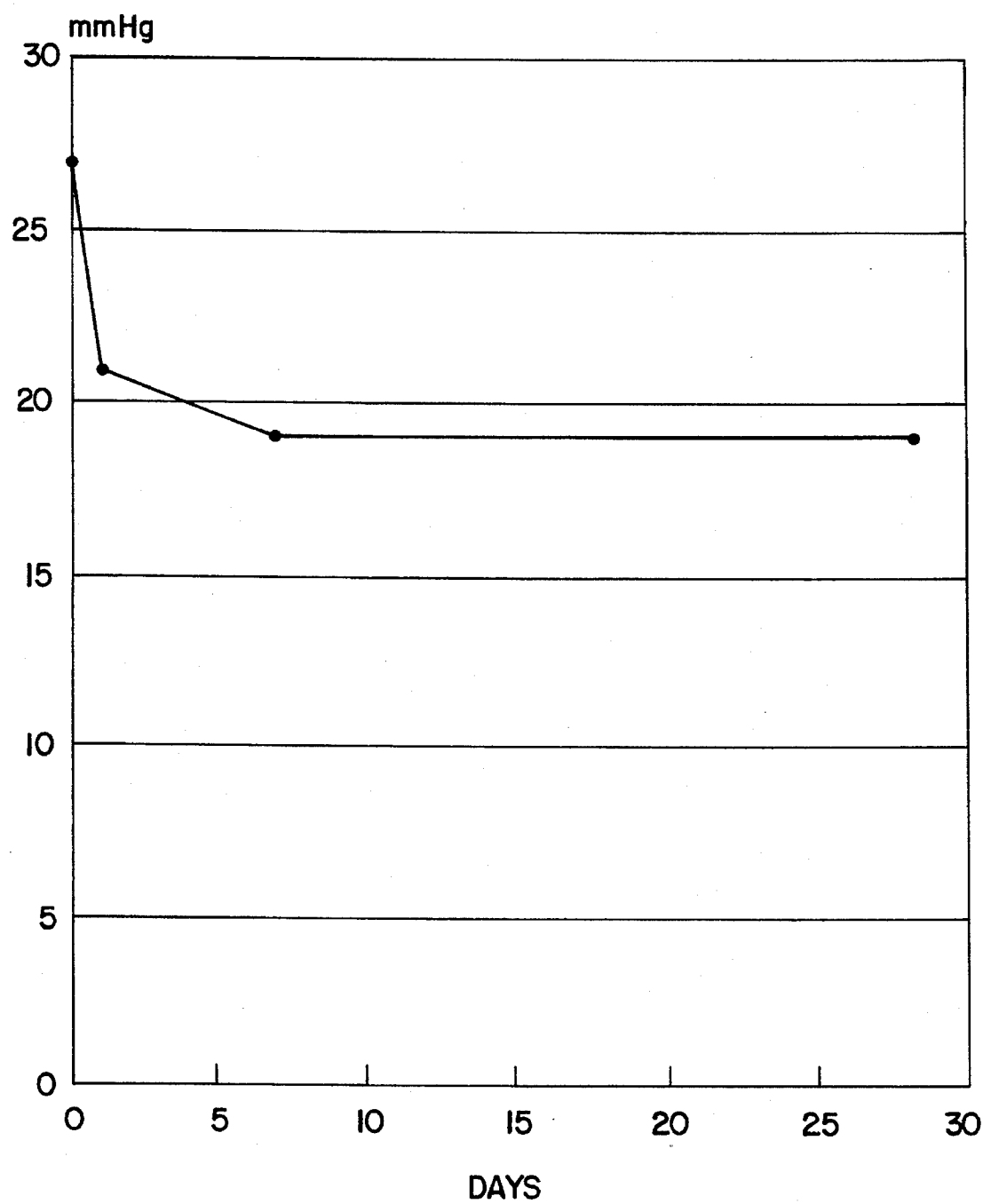
FIG. 1 is a graph of the average intraocular pressure of a group patients treated with the opthalmic solution according to the invention.

In a 28-day clinical study the effectiveness and acceptability of an aqueous ophthalmic solution containing 5% sorbitol was tested on 23 patients having increased intraocular pressure which had been diagnosed for the first time or had previously been untreated. The test preparation was administered twice daily at intervals of about 12 hours, by the application of 1 drop into each eye.

Method:

Testing procedure

Within the course of the test there were four investigation times:

1. Initial investigation before entry into the trial
2. First day of treatment
3. Seventh day of treatment 4. Twenty-eighth day of treatment At each of these investigation times, a daily profile of the internal pressure of the eye was drawn up, using a Goldmann applanation tonometer in order to test the effectiveness. The measurements were taken after 0, 2, 4 and 8 hours on the right eye. At the same time the pupil size of the right eye was measured using a millimeter ruler under standard dimmed lighting and with fixed focus on a remote object. In order to detect systemic side effects, the blood pressure and heart rate of the seated patient were also measured. The local acceptability of the preparation was determined by subjective evaluation of the patient in terms of the degree of intensity of the feeling of a foreign object, itching and burning, the objective ocular acceptability was evaluated by slit-lamp examination of the eyelid, conjunctiva and cornea on the left eye. Particular attention was paid to the presence of erythema and oedema on the eyelid and conjunctiva and oedema and erosion of the cornea.

Within the scope of the initial examination, a perimetric investigation was carried out to exclude any damage to the field of vision.

Results:

Influence of the preparation on intraocular pressure:

Even after one day of treatment the intraocular pressure went down from an average starting level of 27 mm Hg to an average level of 21 mm Hg. The greatest fall in pressure was found 2 hours after administration, and 8 hours after administration the starting levels had not yet been re-attained. After 28 days, before the morning application there was an average 23% fall in intraocular pressure compared with hour 0 on the first day of treatment, and an average 29% fall in intraocular pressure 2 hours after the morning administration. At the end of the 28-day treatment period the average intraocular pressure was 19 mm Hg.

Legend to FIG. 1:

The FIGURE shows the graph of the average intraocular pressure of a group of 23 patients with intraocular hypertension throughout a 28-day treatment by topical application of an aqueous ophthalmic solution containing 5% sorbitol. One drop of the solution was administered to each eye twice a day at intervals of 12 hours. After a significant fall in the pressure level during the first day of treatment, a constant average level of 19 mm Hg is achieved from the 7th day onwards.

Tolerance and side effects:

Measurement of the pupil diameter showed no effect caused by application of the ophthalmic solution. The average pupil diameter remained constant throughout the entire trial period. No miosis or mydriasis was detected in any of the patients.

The systolic and diastolic blood pressure levels and the heart rate were unaffected by the application of the eyedrops, nor were any other systemic side effects observed.

The results of the slit-lamp examination of the eyelid, conjunctiva and cornea and questioning of the patients as to any subjective discomforts such as itching, burning or a feeling of a foreign body yielded only slight effects, in both number and extent, comparable with other ophthalmic agents administered locally.

The present invention thus relates to an ophthalmic solution for topical application to the eye for lowering increased intraocular pressure of aqueous humour, which contains a quantity of a polyhydroxyalcohol such as sorbitol, mannitol, inositol or xylitol effective at lowering the intraocular pressure of aqueous humour, or mixtures of said substances, in a carrier which is tolerated by the eye, the use thereof and processes for preparing it.

The invention further relates to the use of a polyhydroxyalcohol such as sorbitol, mannitol, inositol or xylitol for preparing an ophthalmic solution for topical application to the eye in order to reduce an increased intraocular pressure of aqueous humour, characterised in that the polyhydroxyalcohol is incorporated in a carrier which is tolerated by the eye.

In a preferred embodiment, the ophthalmic solution contains only one of the polyhydroxyalcohols sorbitol, mannitol, inositol or xylitol as the single active substance.

The concentration of the polyhydroxyalcohol in the ophthalmic solution is between 0.5 and 10% by weight, but preferably 3 to 7% by weight. A concentration of active substance in the ophthalmic solution of 3 to 5.4% is particularly preferred.

A sterile aqueous solution may, for example, be used as the carrier which is tolerated by the eye. The aqueous solution is adjusted to a physiologically acceptable pH of 6 to 8 by the addition of a suitable buffer such as boric acid, sodium tetraborate, sodium monohydrogen phosphate, sodium dihydrogen phosphate or citric acid. The solution may further contain excipients known to those skilled in the art, e.g. preservatives such as benzalkonium chloride, surfactants, liposomes or polymers such as for example methylcellulose, polyvinylalcohol or polyvinylpyrrolidone.

The ophthalmic solution is used for topical application to the eye in order to lower increased intraocular pressure of aqueous humour. Since disorders of the intraocular blood-water barriers which result in an increase in the intraocular pressure of aqueous humour frequently occur after intraocular operations such as trabeculectomy or after cataract operations, the ophthalmic solution is particularly suitable for topical application to the eye after intraocular operations.

In the overwhelming majority of cases, increased intraocular pressure occurs in conjunction with glaucoma. For this reason the ophthalmic solution according to the present invention may also be used in conjunction with other drugs, but particularly with anti-glaucoma agents such as for example carboanhydrase inhibitors, pilocarpine, $\alpha_2$-adrenergic compounds such as clonidine, 2-amino-6-allyl-4,5,7,8-tetrahydro-6H-thiazolo[5,4-d]azepine, (-)-2-amino-6-n-propylamino-4,5,6,7-tetrahydrobenzothiazole and phenylephrine and the derivatives thereof, for the topical treatment of increased intraocular pressure of aqueous humour.

The ophthalmic solution is produced by known methods by mixing or dissolving the active substance and the conventional pharmaceutical excipients in the carrier which is tolerated by the eye and will now be explained with reference to the following Examples, in which the compositions specified are not intended to restrict the invention.

EXAMPLE 1:
Recipes for sorbitol eyedrops (composition g/100 ml):
Unless otherwise stated, the solutions specified are euhydric (pH 6.8–7.1)
and eutonic [t: − (290–310 mosmol)].

| | | | | | | | | |
|---|---|---|---|---|---|---|---|---|
| Sorbitol | 7.00 1) | 5.20 | 3.00 2) | 2.00 3) | 4.75 | 3.00 | 1.00 | 0.60 |
| Common Salt | | | | | | 0.30 | | |
| Boric Acid | | | 1.25 | | | | | |
| Na-tetraborate | | | 0.15 | | | | | |
| Na-hydrogen phosphate | | | | | 0.10 | 0.10 | 1.00 | |
| Na-dihydrogen phosphate | | | | | 0.10 | 0.10 | 1.00 | 2.00 |
| Citric Acid | | | | | | | | 0.20 |
| Distilled water | ad 100 | + | + | + | + | + | + | + |
| Preservative: q.s. | + | + | + | + | + | + | + | + |

1) hypertonic
2) hypotonic
3) slightly acidic

What is claimed is:

1. A method for lowering the intraocular pressure of the aqueous humor in a host suffering from elevated intraocular pressure, said method comprising topically administering to the eye of said host an ophthalmic solution comprising a quantity of a polyhydroxyalcohol which is effective for lowering the intraocular pressure of aqueous humor, and a carrier tolerated by the eye, wherein the polyhydroxyalcohol is selected from the group consisting of sorbitol, mannitol, inositol and xylitol.

2. The method according to claim 1, wherein the polyhydroxyalcohol is present in the ophthalmic solution in a concentration of between 0.5 and 10% by weight.

3. The method according to claim 1, wherein the polyhydroxyalcohol is present in the ophthalmic solution in a concentration of between 3 and 7% by weight.

4. The method according to claim 1, wherein the polyhydroxyalcohol is present in the ophthalmic solution in a concentration of between 3 and 5.4% by weight.

5. The method according to claim 1, wherein the polyhydroxyalcohol is sorbitol.

6. The method according to claim 1, wherein the carrier tolerated by the eye is an aqueous solution.

7. The method according to claim 6, wherein the aqueous solution has a pH of between 6 and 8.

8. The method according to claim 1, wherein the elevated intraocular pressure is due to trabeculectomy or cataract removal.

9. The method according to claim 1, which method additionally comprises administering topically an anti-glaucoma agent to the eye of the host.

* * * * *